(12) United States Patent
Lang et al.

(10) Patent No.: US 6,949,257 B2
(45) Date of Patent: Sep. 27, 2005

(54) PHARMACEUTICAL COMPOSITIONS

(75) Inventors: Steffen Lang, Reinach (CH); Kurt Liechti, Oberwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/379,345

(22) Filed: Mar. 4, 2003

(65) Prior Publication Data

US 2003/0152626 A1 Aug. 14, 2003

Related U.S. Application Data

(63) Continuation of application No. 10/119,549, filed on Apr. 10, 2002, now abandoned, which is a continuation of application No. 09/722,766, filed on Nov. 20, 2000, now abandoned, which is a continuation of application No. PCT/EP99/03623, filed on May 26, 1999.

(30) Foreign Application Priority Data

May 26, 1998 (GB) .............................. 9811200
Aug. 19, 1998 (GB) .............................. 9818105

(51) Int. Cl.[7] .......................... A61K 9/10; A61K 9/66; A61K 47/00; A61K 31/435; A61K 31/445
(52) U.S. Cl. ...................... 424/455; 424/400; 424/439; 424/450; 514/183; 514/277; 514/279; 514/299; 514/311; 514/315; 514/317; 514/319; 514/320; 514/323; 514/329; 514/330
(58) Field of Search ................................ 424/455, 450; 514/311, 315, 937, 938

(56) References Cited

U.S. PATENT DOCUMENTS

| 5,310,743 A | | 5/1994 | Schilling et al. ............ 514/311 |
| 5,342,625 A | * | 8/1994 | Hauer et al. ................. 424/443 |
| 5,646,144 A | | 7/1997 | Schilling et al. ............ 514/241 |
| 5,730,998 A | | 3/1998 | De Lacharriere et al. ... 424/443 |
| 5,744,156 A | | 4/1998 | De Lacharriere et al. ... 424/445 |
| 5,886,011 A | | 3/1999 | Tanoue et al. .............. 514/320 |
| 5,952,004 A | * | 9/1999 | Rudnic et al. .............. 424/455 |
| 5,965,562 A | | 10/1999 | Ofner et al. ................ 514/259 |

FOREIGN PATENT DOCUMENTS

| EP | 120 262 | 10/1984 |
| EP | 707 006 | 4/1996 |
| GB | 2270842 | 3/1994 |
| GB | 2278780 | 12/1994 |
| GB | 2308545 | 7/1997 |
| WO | WO 94/00123 | 1/1994 |
| WO | WO 97/22358 | 6/1997 |
| WO | WO 97/25977 | 7/1997 |
| WO | WO 97/45119 | 12/1997 |
| WO | WO 99/61025 | 12/1999 |

OTHER PUBLICATIONS

Linder, Derwent Abstracts, 1994–008363 [02], (WO 94/00123–Jan. 6, 1994).
Fries, Derwent Abstracts, 1984–214059 [35], (EP 120 262–Jul. 13, 1988).
Skagerlind et al., "Surfactant Interference on Lipase Catalysed Reactions in Microemulsions", J. Chem. Technol. Biotechnol., vol. 54, No. 3, pp. 277–282 (1992).
Wells et al., "Effect of Surfactants on Release of a Highly Water–Soluble Medicinal Compund from an Inert, Heterogeneous Matrix", J. Pharm. Sci., vol. 81, No. 5, pp. 453–457 (1992).
Drewe et al., "Enhancement of the Oral Absortion of Cyclosporin in Man", Br. J. Clin. Pharmacol., vol. 34, No. 1, pp. 60–64 (1992).
Aungst, "Novel Formulation Strategies for Improving Oral Bioavailability of Drugs with Poor Membrane Permeation or Presystemic Metabolism", J. Pharm. Sci., vol. 82, No. 10, pp. 979–987 (1993).
Kondo et al., "Improved Oral Absorption of Entreric Coprecipitates of a Poorly Soluble Drug", J. Pharm. Sci., vol. 83, No. 4, pp. 566–570 (1994).
Constantinides et al., "Formulation and Intestinal Absorption Enhancement Evaluation of Water–In–Oil Microelmulsions Incorporating Medium–Chain Glycerides", Pharm. Res., vol. 11, No. 10, pp. 1385–1390 (1994).
Constantinides, "Lipid Microemulsions for Improving Drug Dissolution and Oral Absorption: Physical and Biopharmaceutical Aspects", vol. 12, No. 11, pp. 1561–1572 (1995).
Ho et al., "Preparation of Microemulsions Using Polyglycerol Fatty Acid Esters as Surfactant for the Delivery of Protein Drugs", J. Pharm. Sci., vol. 85, No. 2, pp. 138–143 (1996).
Avramiotis et al., "Structural and Dynamic Properties of Lecithin–Alcohol Based w/o Microemulsions: A Luminescence Quenching Study", J. Colloid Interface Sci., vol. 194, No. 2, pp. 326–331 (1997).
Aramaki et al., "Effect of Temperature on the Phase Behavior of Ionic–Nonionic Microemulsions", J. Colloid Interface Sci., vol. 196, No. 1, pp. 74–78 (1997).
Gonsalves et al., "Synthesis and Surface Characterization of Functionalized Polylactide Copolymer Microparticles", Biomaterials, vol. 19, No. 16, pp. 1501–1505 (1998).

* cited by examiner

Primary Examiner—Thurman K. Page
Assistant Examiner—Simon J. Oh
(74) Attorney, Agent, or Firm—E. Jay Wilusz

(57) ABSTRACT

Spontaneously dispersible pharmaceutical compositions comprising a piperidine, e.g. 1-acylpiperidine Substance P Antagonist and its use in the treatment of CNS disorders, e.g. depression and social phobia, and respiratory diseases, e.g. asthma and chronic bronchitis.

10 Claims, No Drawings

PHARMACEUTICAL COMPOSITIONS

This application is a continuation of U.S. patent application Ser. 10/119,549, filed Apr. 10, 2002 now abandoned, which is a continuation of U.S. patent application Ser. No. 09/722,766, filed Nov. 20, 2000 now abandoned which is a continuation of International Application No. PCT/EP99/03623, filed May 26, 1999, the contents of which are incorporated herein by reference.

The present invention relates to novel pharmaceutical compositions in which the active agent is a piperidine substance P antagonist, in particular a N-benzoyl-2-benzyl-4-(azanaphthoyl-amino) piperidine, useful for treatment and prevention of e.g. central nervous system disorders, e.g. depression, social phobia, or respiratory diseases, e.g. asthma and chronic bronchitis. 1-Acylpiperidine substance P antagonists are a class of compounds described e.g. in published European patent EP 0532456B1, the contents of which publication is incorporated herein by reference. Similarly, N-benzoyl-2-benzyl-4-(azanaphtyoyl-amino) piperidines and their activity as Substance P Antagonists are described in published European patent application EP 0707006A, the contents of which application is incorporated herein by reference.

Piperidine substance P antagonists, such as disclosed in EP 0532456B1 and EP 0707006A, present highly specific difficulties in relation to administration generally and galenic compositions in particular, including in particular problems of drug bioavailability and variability in inter- and intra-patient dose response, necessitating development of a non-conventional dosage form.

In accordance with the present invention it has now surprisingly been found that stable pharmaceutical compositions with Piperidine substance P antagonists, having particularly interesting bioavailability characteristics and reduced variability in inter- and intra-subject bioavailability parameters, are obtainable. These novel compositions have been found to meet or substantially reduce the difficulties encountered previously. It has been shown that the compositions in accordance with the present invention may enable effective dosaging with concomitant enhancement as well as reduced variability of resorption/bioavailability levels for and between individual patients. Thus, the invention may achieve effective therapy with tolerable dosage levels of such Piperidine substance P antagonists, and may permit closer standardization and optimization of daily dosage requirements for each individual. Consequently, occurrence of potential undesirable side-effects is diminished and overall cost of therapy may be reduced.

In one aspect the present invention provides a spontaneously dispersible pharmaceutical composition comprising a Piperidine substance P antagonist, hereinafter also referred to as the active agent.

Such spontaneously dispersible pharmaceutical compositions are preferably in liquid form, or are produced from at least one liquid component and preferably are micellar precursors.

The "term spontaneously dispersible pharmaceutical composition" as used herein is defined as a system that is capable of producing colloidal structures, e.g. solid or preferably liquid particles, e.g. droplets and/or nanoparticles, and/or micellar compositions, e.g. aqueous micelles, e.g. of up to 1000 nm in diameter, when diluted with an aqueous medium, for example, in water, for example on dilution at a dilution ratio e.g. 1:10 of composition to water, or in gastric juices, e.g. simulated conditions after oral application at a similar dilution ratio at e.g from 15 to 37 degrees Centigrade. The spontaneously dispersible pharmaceutical compositions are hereinafter also referred to as compositions of the invention. The colloidal structures may form spontaneously or substantially spontaneously when the components of the composition of the invention are brought into contact with an aqueous medium, e.g. by simple shaking by hand for a short period of time, for example for 10 seconds. The compositions of the invention are thermodynamically stable, e.g. for at least 15 minutes or up to 4 hours, even to 24 hours. Typically, they contain dispersed structures of a mean diameter less than about 300 nm (3,000 Å), e.g. less than about 200 nm (2,000 Å) as measured by standard light scattering techniques, e.g. using a Malvern Zetasizer 3000. Naturally the particles of mean diameter greater than 200 nm may be present, but these are preferably less than 50% by weight, e.g. less than 10–20% per weight, of the total. Preferably they comprise droplets or nanoparticles having a mean diameter of less than about 150 nm (1,500 Å), typically less than 100 nm (1,000 Å), generally greater than 5 nm (50 Å). Alternatively, the spontaneously dispersible pharmaceutical compositions may form upon dilution simultaneously a mixture comprising micelles and nanoparticles. The micelles may be essentially monophasic and substantially non-opaque, i.e. transparent or opalescent when viewed by optical microscopic means. It was found that the proportion of nanoparticles present may be temperature dependent but still adequate bioavailability characteristics may be obtained.

In another aspect the present invention provides a spontaneously dispersible pharmaceutical composition comprising a piperidine substance P antagonist as the active agent, and a carrier medium comprising
1) a hydrophilic component, and
2) a surfactant.

Preferably such spontaneously dispersible pharmaceutical compositions are for oral administration. Conveniently the Piperidine substance P antagonist, is water insoluble, e.g. has a solubility of below 0.001%, e.g. 0.001 to 0.0001%. Conveniently the active agents are used in free base form.

The active agents may show Substance P antagonistic activity as indicated in standard in vitro or in vivo tests e.g. as disclosed in the above-mentioned European filings.

The piperidine may be a piperidine derivative which is an analogue or may be poly (e-g. di or tri-) substituted. The active agents include not only those disclosed in the above mentioned European filings but also analogues for example a) 1-[2-[3-(3,4-Dichlorophenyl)-1-[(3-(1-isopropoxyphenyl)acetyl]piperidin-3-yl]ethyl]-4-phenyl-1-azoniabicyclo[2.2.2]octane,
b) (2S-cis)-N-[(2-methoxyphenyl)methyl]-2-phenyl-)-piperidinamine [CP-99994],
c) cis-3-((3-methyl-5-trimethylsilyl)benzyloxy)-2-phenyl piperidine,
d) 4-phenyl-4-((1-(3,5-bis(trifluoromethyl)phenyl)-2-hydroxyethoxy)methyl)piperidine [L-733060],
e) 2-phenyl-3-(3,5-bis(trifluoromethyl)benzyloxy) piperidine [L-733060],
f) (R)-3-(1H-indol-3-yl)-1-[N-(2-methoxybenzyl) acetylamino]-2-[N-(2-(4-(piperidin-1-yl)piperidin-1-yl) acetyl)amino]propane,
g)-3-(1H-indol-3-yl)-1-[N-(2-methoxybenzyl)acetylamino]-2-[N-(2-(4-(piperidin-1-yl)piperazin-1-yl)acetyl)amino] propane,
h) (2-Methoxy-5-(5-trifluoromethyl-tetrazol-1-yl)-benzyl)-(2S-phenyl-1-piperidin-3S-yl)-amine [GR-205171],
i) (−)-(B)-cis-4-[1-[3,5-bis(trifluoromethyl)benzoyl]-2-(phenylmethyl)-4-piperidin yl]-N-(2,6-dimethylphenyl)-1-piperazine acetamide,
including salts thereof.

The active agents are preferably 1-acylpiperidine substance P antagonists e.g. as claimed in EP 0532456 B. Preferred compounds of the invention are the compounds of EP 0707006 A, e.g. N-benzoyl-2-benzyl-4-(azanaphthoyl-amino) piperidines, and most preferably (2R,4S)-N-(1-(3,5-bis(trifluoromethyl)-benzoyl)-2-(4-chlorobenzyl)-4-piperidinyl)-quinoline-4-carboxamide, hereinafter referred to as Compound A, as disclosed in EP 707 006.

The composition of the invention may also comprise a carrier medium containing further components. Typical further components of the compositions of the invention are, e.g. described in Fiedler, H. P. "Lexikon der Hilfsstoffe für Pharmazie, Kosmetik und angrenzende Gebiete", Editio Cantor, D-7960 Aulendorf, 4th revised and expanded edition (1996).

In accordance with the present invention the active agent may be present in an amount by weight of up to about 20% by weight of the composition of the invention, e.g. from about 0.05% by weight. The active agent are preferably present in an amount of 0.5 to 15% by weight of the composition, for example about 1 to 10%, preferably 1.5 to 2%.

The hydrophilic component typically has a solubility in water of at least 1 g/100 ml or more, e.g. at least 5 g/100 ml at 25 degrees centigrade. It preferably provides for fast mixing of an active agent with water. Such mixing may be determined by routine experimentation, for example by various chromatography methods, e.g. Gas Chromatography (GC). Conveniently the hydrophilic component may also be miscible with an organic solvent, e.g. ether. Preferably the hydrophilic component may be an alcohol, e.g. a water miscible alcohol, e.g. absolute ethanol, or glycerol. Other alcohols include glycols, e.g. any glycol obtainable from an oxide such as ethylene oxide, e.g. 1,2-propylene glycol. Other examples are polyols, e.g. a polyalkylene glycol, e.g. poly($C_{2-3}$)alkylene glycol. A typical example is a polyethylene glycol, e.g. of a preferred molecular weight of 200–1000 daltons, more preferably, 200–400 daltons, especially 400. Alternatively the hydrophilic component may preferably comprise an N-alkylpyrolidone, e.g. N-($C_{1-14}$alkyl)pyrolidone, e.g. N-methylpyrolidone, tri($C_{1-4}$alkyl) citrate, e.g. triethylcitrate, dimethylisosorbide, ($C_5$-$C_{13}$) alkanoic acid, e.g. caprylic acid or propylene carbonate. Most preferred is triethylcitrate or propylene glycol.

The hydrophilic component may comprise a main or sole component, e.g. an alcohol, e.g. $C_{1-4}$-alcohol, e.g. ethanol, or alternatively a co-componente.g which may be selected from partial lower ethers or lower alkanols. Especially preferred partial ethers are those known and commercially available, for example Transcutol (which has the formula $C_2H_5$—[O—$(CH_2)_2$]$_2$—OH), Glycofurol (also known as tetrahydrofurfuryl alcohol polyethylene glycol ether), or lower alkanols such as ethanol. Preferred alkanol components include ethanol, 1,2-propylene glycol or a polyethylene glycol, e.g. of a molecular weight of 100 to 600 daltons, e.g. polyethylene glycol 400. When present ethanol may comprise 0, e.g 1 to, to 60% by weight of the hydrophilic component; preferably 20 to about 55% by weight and more preferably about 40 to about 50% by weight. The hydrophilic component may conveniently contain ethanol as sole component. The ratio of hydrophilic component to hydrophilic co-component is typically from about 0.5:1 to about 2:1.

The hydrophilic component may comprise 5 to 50% by weight of the composition of the invention, e.g. 10 to 50%; preferably 15 to 40% by weight, more preferably about 20 to about 30% by weight, e.g. from 15 to 35% by weight.

Examples of suitable surfactants, e.g. preferably surfactants of high HLB value, e.g. HLB>10, for use in this invention are:

(i) Reaction products of a natural or hydrogenated castor oil and ethylene oxide, i.e. polyoxyethylene glycolated natural or hydrogenated vegetable oils, for example polyoxyethylene glycolated natural or hydrogenated castor oils. The natural or hydrogenated castor oil may be reacted with ethylene oxide in a molar ratio of from about 1:35 to about 1:60, with optional removal of the polyethyleneglycol component from the products. Various such surfactants are commercially available. The polyethyleneglycol-hydrogenated castor oils available under the trade name CREMOPHOR are especially suitable. Particularly suitable are CREMOPHOR RH 40, which has a saponification number of about 50 to 60, an acid number less than about 1, a water content (Fischer) less than about 2%, an $n_D^{60}$ of about 1.453 to 1.457 and an HLB of about 14 to 16; and CREMOPHOR RH 60, which has a saponification number of about 40 to 50, an acid number less than about 1, an iodine number of less than about 1, a water content (Fischer) of about 4.5 to 5.5%, an $n_D^{25}$ of about 1.453 to 1.457 and an HLB of about 15 to 17. An especially preferred product of this class is CREMOPHOR RH40. Also suitable are polyethyleneglycol castor oils such as that available under the trade name CREMOPHOR EL, which has a molecular weight (by steam osmometry) of about 1630, a saponification number of about 65 to 70, an acid number of about 2, an iodine number of about 28 to 32 and an $n_D^{25}$ of about 1.471 and an HLB value of about 12 to 14. Similar or identical suitable products which may also be used are the various tensides available under the trade names NIKKOL (e.g. NIKKOL HCO-40 and HCO-60), MAPEG (e.g. MAPEG CO-40h), INCROCAS (e.g. INCROCAS 40), and TAGAT (for example polyoxyethylene-glycerol-fatty acid esters e.g. TAGAT RH 40. A preferred polyethoxylated glyceride is TAGAT TO, a polyoxyethylene-glycerol-trioleate having a HLB value of 11.3. These surfactants are further described in Fiedler loc. cit., incorporated herein by reference.

(ii) Related products that belong to the class of polyoxyethylene alkyl ethers are available under the tradename BRIJ, e.g. Brij 35 which has an HLB value of about 16.9.

(iii) Polyoxyethylene-sorbitan-fatty acid esters (also called polysorbates), e.g. of from 4 to 25 alkylene moieties, for example mono- and tri-lauryl, palmityl, stearyl and oleyl esters of the type known and commercially available under the trade name TWEEN (Fiedler, loc.cit. p.1300–1304, incorporated herein by reference) including the products TWEEN 20 [polyoxyethylene(20)sorbitanmonolaurate],
21 [polyoxyethylene(4)sorbitanmonolaurate],
40 [polyoxyethylene(20)sorbitanmonopalmitate],
60 [polyoxyethylene(20)sorbitanmonostearate],
65 [polyoxyethylene(20)sorbitantristearate],
80 [polyoxyethylene(20)sorbitanmonooleate],
81 [polyoxyethylene(5)sorbitanmonooleate],
85 [polyoxyethylene(20)sorbitantrioleate].

Especially preferred products of this class are TWEEN 40 and TWEEN 80.

(iv) Polyoxyethylene fatty acid esters, for example polyoxyethylene stearic acid esters of the type known and commercially available under the trade name MYRJ (Fiedler, loc. cit., 2, p.834–835, incorporated herein by reference). An especially preferred product of this class is MYRJ 52 having a $n_D^{50}$ of about 1.1, a melting point of about 40 to 44° C., an HLB value of about 16.9, an acid value of about 0 to 1 and a saponification no. of about 25 to 35. Other related products include polyethoxylated saturated hydroxy fatty acids which may be produced by reacting a saturated hydroxy fatty acid, e.g. $C_{18}$ to $C_{20}$ with e.g. ethylene oxide or polyethylene glycol. Suitable examples for the present invention include are known and commercially available, e.g. from the BASF company under the trade mark Solutol. Especially preferred is Solutol HS15 which is known, e.g. from the BASF technical leaflet MEF 151E (1986), to comprise of about 70% polyethoxylated 12-hydroxystearate by weight and about 30% by weight unesterified polyethylene glycol component. Solutol HS 15 has a hydrogenation value of 90 to 110, a saponification value of 53 to 63, an acid number of maximum 1, and a maximum water content of 0.5% by weight.

(v) Polyoxyethylene-polyoxypropylene co-polymers and block co-polymers, for example of the type known and commercially available under the trade names PLURONIC, EMKALYX and POLOXAMER (Fiedler, loc. cit., 2, p. 959, incorporated herein by reference). An especially preferred product of this class is PLURONIC F68, having a melting point of about 52° C. and a molecular weight of about 6800 to 8975. A further preferred product of this class is POLOXAMER 188, which has an HLB value of about 29.

(vi) Propylene glycol mono- and di-fatty acid esters such as propylene glycol dicaprylate (also known and commercially available under the trade name MIGLYOL 840), propylene glycol dilaurate, propylene glycol hydroxystearate, propylene glycol isostearate, propylene glycol laurate, propylene glycol ricinoleate, propylene glycol stearate and so forth (Fiedler, loc. cit., 2, p. 808–809, incorporated herein by reference). Propylene glycol mono $C_8$ esters include Sefsol 218 (Nikko Chemicals) and Capryol 90 (Gattefossé).

(vii) Tocopherol esters, e.g. tocopheryl acetate and tocopheryl acid succinate (HLB of about 16).

Further ionic surfactant classes not represented by the categories described above include (i) Docusate salts, for example dioctylsulfosuccinate or related compounds, for example di-[2-ethylhexyl]-succinate (Fiedler, loc. cit. 1, p. 107–108, incorporated herein by reference).

(ii) Phospholipids, in particular lecithins (Fiedler, loc. cit, 2, p. 943–944, incorporated herein by reference). Suitable lecithins include, in particular, soya bean lecithins.

The surfactant selected preferably has a hydrophilic-lipophilic balance (HLB) of at least 10, for example Cremophor, e.g. Cremophor RH40. A group of surfactants comprises those with a polyoxyethylene moiety.

The surfactant may comprise 5 to 80% by weight of the composition of the invention; preferably 10 to 70% by weight, more preferably 20 to 60% by weight and even more preferably between about 40% and 55% by weight.

The compositions of the invention may further comprise a lipophilic phase or lipophilic component. These compositions may be capable of producing emulsions as colloidal structures, preferably an aqueous microemulsion as a micelle, upon mixing with an aqueous medium.

In another aspect the present invention provides a spontaneously dispersible pharmaceutical composition, preferably in the form of a microemulsion preconcentrate, comprising a piperidine substance P antagonist.

In yet another aspect the present invention provides a spontaneously dispersible pharmaceutical composition, preferably in the form of a microemulsion preconcentrate, comprising a piperidine substance P antagonist, e.g. Compound A, and a carrier medium comprising
1) a hydrophilic phase,
2) a lipophilic phase, and
3) a surfactant.

Such compositions of the invention may be in the form of "microemulsion preconcentrates" of the type providing o/w (oil-in-water) microemulsions. A "microemulsion preconcentrate" is defined in this specification as being a composition which spontaneously forms a microemulsion in an aqueous medium, for example, in water, for example on dilution of 1:1 to 1:10, e.g. 1:10 or in the gastric juices after oral application. Typically, a "microemulsion" is a slightly opaque, opalescent, non-opaque or substantially non-opaque colloidal dispersion that is formed spontaneously or substantially spontaneously when its components are brought into contact with an aqueous medium. A microemulsion is thermodynamically stable and contains dispersed particles of a mean diameter less than about 2000 Å. Generally microemulsions comprise droplets or liquid nanoparticles having a mean diameter of less than about 1500 Å; typically less than 100 nm, generally greater than 10 nm, and stable over periods in excess of 24 hours.

Naturally, such compositions of the invention comprising a hydrophilic phase, lipophilic phase and surfactant may, e.g. before dilution, e.g. be preferably a hydrophilic component, lipophilic component and surfactant in the form of essentially a single phase system, e.g. a w/o microemulsion or other micellar composition.

Such compositions of the invention additionally containing an aqueous phase, preferably water, may be in the form of a microemulsion.

The lipophilic component, when present, may preferably be characterized by a low HLB value of less than 10, e.g. up to 8, and may comprise (i) medium chain fatty acid triglycerides, (ii) mixed mono-, di-, tri-glycerides, (iii) trans-esterified ethoxylated vegetable oils, (iv) mixtures of mono- and di-glycerides, or pure or substantially pure mono- or cdi-glycerides, (v) sorbitan fatty acid esters, (vi) pentaerythriol fatty acid esters and the like, and (vii) other suitable components such as glycerol triacetate and the like. Some of these, e.g. (iii) to (vii), display surfactant-like behaviour and may also be termed co-surfactants.

(i) Suitable medium chain fatty acid triglycerides are neutral oils, e.g. neutral plant oils, in particular fractionated coconut oils, for example those known and commercially available under the trade names Captex, Myritol, Capmul, Captex, Neobee and Mazol; Miglyol 812 being the most preferred. Miglyol 812 is a fractionated coconut oil comprising caprylic-capric acid triglycerides and having a molecular weight=about 520 daltons. Fatty acid composition=$C_6$ max. about 3%, $C_8$ about 50 to 65%, $C_{10}$ about 30 to 45%, $C_{12}$ max 5%; acid no.=about 0.1; saponification no. about 330 to 345; iodine no.=max 1. Miglyol 812 is available from the Hüls company. These triglycerides are described in Fiedler, loc. cit., vol., p. , incorporated herein by reference.

(ii) Mixed mono-, di-, tri-glycerides preferably comprise mixtures of $C_8$ to $C_{10}$ or $C_{12-20}$ fatty acid mono-, di- and tri-glycerides, especially mixed $C_{16-18}$ fatty acid mono-, di- and triglycerides. The fatty acid component of the mixed mono-, di- and tri-glycerides may comprise both saturated and unsaturated fatty acid residues. Preferably however they are predominantly comprised of unsaturated fatty acid residues; in particular $C_{18}$ unsaturated fatty acid residues. Suitably the mixed mono-, di-, triglycerides comprise at least 60%, preferably at least 75%, more preferably at least 85% by weight of a $C_{18}$ unsaturated fatty acid (for example linolenic, linoleic and oleic acid) mono-, di- and tri-glycerides. Suitably the mixed mono-, di-, tri-glycerides comprise less than 20%, for example about 15% or 10% by weight or less, saturated fatty acid (for example palmitic and stearic acid) mono-, di- and tri-glycerides. Mixed mono-, di-, tri-glycerides are preferably predominantly comprised of mono- and di-glycerides; for example mono- and di-glycerides comprise at least 50%, more preferably at least 70% based on the total weight of the lipophilic phase or component. More preferably, the mono- and di-glycerides comprise at least 75% (for example about 80% or 85% by weight of the lipophilic component. Preferably monoglycerides comprise from about 25 to about 50%, based on the total weight of the lipophilic component, of the mixed mono-, di-, tri-glycerides. More preferably from about 30 to about 40% (for example 35 to 40%) monoglycerides are present. Preferably diglycerides comprise from about 30 to about 60%, based on the total weight of the lipophilic component, of the mixed mono-, di-, tri-glycerides. More preferably from about 40 to about 55% (for example 48 to 50%) diglycerides are present. Triglycerides suitably comprise at least 5% but less than about 25%, based on the total weight of the lipophilic component, of the mixed mono-, di-, tri-glycerides. More preferably from about 7.5 to about 15% (for example from about 9 to 12%) triglycerides are present. Mixed mono-, di-, tri-glycerides may be prepared by admixture of individual mono-, di- or tri-glycerides in appropriate relative proportion. Conveniently however they comprise transesterification products of vegetable oils, for example almond oil, ground nut oil, olive oil, peach oil, palm oil or, preferably, corn oil, sunflower oil or safflower oil and most preferably corn oil, with glycerol. Such transesterification products are generally obtained as described in GB 2 257 359 or WO 94/09211, the contents of which are incorporated herein by reference. Preferably some of the glycerol is first removed to give a "substantially glycerol free batch" when soft gelatine capsules are to be made. Purified transesterification products of corn oil and glycerol provide particularly suitable mixed mono-, di-, and tri-glycerides hereinafter referred to as "refined oil" and produced according to the description of GB 2 257 359 or WO 94/09211.

(iii) The lipophilic component may alternatively comprise e.g. a pharmaceutically acceptable oil, preferably with an unsaturated component such as a vegetable oil or fish oil. Tile lipophilic component may comprise suitable transesterified ethoxylated vegetable oils such as those obtained by reacting various natural vegetable oils (for example, maize oil, kernel oil, almond oil, ground nut oil, olive oil, soybean oil, sunflower oil, safflower oil and palm oil, or mixtures thereof) with polyethylene glycols that have an average molecular weight of from 200 to 800, in the presence of an appropriate catalyst. These procedures are known and an example is described in U.S. Pat. No. 3,288,824. Transesterified ethoxylated corn oil is particularly preferred. Transesterified ethoxylated vegetable oils are known and are commercially available under the trade name LABRAFIL (H. Fiedler, loc cit, vol 2, page 707, incorporated herein by reference). Examples are LABRAFIL M 2125 CS (obtained from corn oil and having an acid number of less than about 2, a saponification number of 155 to 175, an HLB value of 3 to 4, and an iodine number of 90 to 110), and LABRAFIL M 1944 CS (obtained from kernel oil and having an acid number of about 2, a saponification number of 145 to 175 and an iodine number of 60 to 90). LABRAFIL M 2130 CS (which is a transesterification product of a $C_{12-18}$ glyceride and polyethylene glycol and which has a melting point of about 35 to 40° C., an acid number of less than about 2, a saponification number of 185 to 200 and an iodine number of less than about 3) may also be used. The preferred transesterified ethoxylated vegetable oil is LABRAFIL M 2125 CS which can be obtained, for example, from Gattefossé, Saint-Priest Cedex, France.

(iv) Mono-, di-and mono/diglycerides, e.g. suitable $C_8$ to $C_{10}$ fatty acid mono-, di- and tri-glycerides include Capmul MCM, Akoline MCM (from the Karlshamns company), Imwitor 308 and Imwitor 988 (from the Contensio company), which have an HLB value of about 3.8 (from the Contensio company), and especially esterification products of caprylic or capric acid with glycerol. Preferred products are of this class are e.g. those comprising or essentially consisting of caprylic/capric acid mono- and di-glycerides. $C_8$ to $C_{10}$ mono-, di-glycerides having 6 to 10 mol-% polyoxyethylene groups, e.g. Softigen 767 (available from Contensio Chemicals). Monoglycerides, e.g. monooleate, glycerol monopalmitate and glycerol monostearate, for example as known and commercially available under the trade names Myvatex, Myvaplex, and Myverol (Fiedler, loc. cit., 2, p. 1044, incorporated herein by reference) and acetylated, e.g. mono- and di-acetylated monoglycerides, for example as known under the trade name Myvacet (Fiedler, loc. cit., 2, p. 1043, incorporated herein by reference). Most preferred is Capmul MCM.

(v) Sorbitan fatty acid esters, e.g. of the type known and commercially available under the trade name Span, for example including sorbitan-monolaureyl ester (HLB 8.6), -monopalmityl ester (HLB 6.7), -monostearyl ester (HLB 4.7), -tristearyl ester (HLB 2.1), -monooleyl ester (HLB 4.3), and -trioleyl esters (HLB 1.8) (Fiedler, loc. cit., 2, p. 1430, incorporated herein by reference).

(vi) Pentaerythriol fatty acid esters and polyalkylene glycol ethers and polyalkylene glycol ethers, for example pentaerythrite-dioleate, -distearate, -monolaurate, -polyglycol ether, and -monostearate as well as pentaerythrite-fatty acid esters (Fiedler, loc. cit., 2, p. 1158–1160, incorporated herein by reference)

(vii) Other suitable components include glycerol triacetate or (1,2,3)-triacetin (Fiedler, loc. cit., 2, p. 1580, incorporated herein by reference); and sterols and derivatives thereof.

When present, the lipophilic component may comprise 5 to 85% by weight of the composition of the invention, e.g. 10 to 85%; preferably 15 to 70% by weight, more preferably about 20 to about 50% by weight. Preferably the relative proportion of hydrophilic component(s), lipophilic component(s) and the surfactant(s) lie within the "microemulsion" region on a standard three way plot graph.

The present applicants also contemplate compositions of the invention in the form of microemulsion preconcentrate which may be free of refined fish oil and/or ethanol and/or transesterified ethoxylated vegetable oil.

The composition of the invention may further include additives or ingredients, for example antioxidants (such as ascorbyl palmitate, butyl hydroxy anisole (BHA), butyl hydroxy toluene (BHT) and tocopherols), antimicrobial agents, enzyme inhibitors, stabilizers, and/or preserving agents. These additives or ingredients may comprise about 0.05 to 5%, preferably 0.05 to 1% by weight of the total weight of the composition of the invention. The compositions of the invention may also include sweetening or flavoring agents in an amount of up to about 2.5 or 5% by weight based on the total weight of the composition of the invention.

In another aspect the invention provides a process for the production of a composition of the invention, which process comprises bringing the active agent and (1) the hydroplilic component, (2) the surfactant, and optionally (3) the lipophilic component into intimate admixture.

When required, the compositions of the invention are preferably compounded in unit dosage form, for example by filling them into orally administrable capsule shells. The capsule shells may be soft or hard gelatine capsule shells. Where the composition is in unit dosage form, each unit dosage will suitably contain from 0.1 and 100 mg active agent, for example 0.1 mg, 1 mg, 5 mg, 10 mg, 15 mg, 25 mg or 50 mg, preferably between 10 and 100 mg of the active agent, more preferably between 10 and 50 mg; for example 15, 20, 25, or 50 mg, more preferably between 5 and 20 mg, most preferably 5 or 10 mg. Such unit dosage forms are suitable for administration 1 to 5 times daily depending upon the particular purpose of therapy, the phase of therapy and the like. However, if desired, the compositions may be in drink solution form and may include water or any other aqueous system, e.g. fruit juice, milk, and the like, to provide e.g. colloidal systems, suitable for drinking, e.g. with a dilution of from about 1:10 to about 1:100.

The compositions of the invention, e.g. those in the examples hereinafter, may show good stability characteristics as indicated by standard stability trials, for example having a shelf life stability of up to one, two or three years, and even longer. The compositions of this invention in form of micellar precursors produce stable aqueous micelles, e.g. for up to one day or longer. One group of compositions of the invention may be of high stability that are capable, on addition to water, of providing aqueous microemulsions having an average particle size of <2,000 Å (200 nm), e.g. <1,500 Å (150 nm).

The compositions of the invention exhibit especially advantageous properties when administered orally; for example in terms of consistency and high level of bioavailability obtained in standard bioavailability trials. These trials are performed in animals e.g. rats or dogs or healthy volunteers using chromatographic methods, e.g. HPLC, or a specific or nonspecific monoclonal kit to determine the level of the active agent in the blood. For example, the composition of Example 5 administered p.o. to dogs may give surprisingly high $C_{max}$ values as detected by ELISA using a specific monoclonal antibody.

Pharmacokinetic parameters, for example absorption and blood levels, also become surprisingly more predictable and problems in administration with erratic absorption may be eliminated or reduced. Additionally the compositions are effective with tensile materials, for example bile salts, being present in the gastro-intestinal tract. That is, the compositions may be fully dispersible in aqueous systems comprising such natural tensides and thus may be capable of providing microemulsion or aqueous micellar systems in situ which are stable and do not exhibit precipitation of the active agent or other disruption of fine particulate structure. The function of the compositions upon oral administration may remain substantially independent of and/or unimpaired by the relative presence or absence of bile salts at any particular time or for any given individual. It also has been found that the compositions of this invention may reduce variability in inter- and intra-patient dose response.

The utility of the compositions of the invention may be observed in standard clinical tests in, for example, known indications of active agent at dosages giving therapeutically effective active agent blood levels. Any increased bioavailability of the compositions of the invention may be observed in standard animal tests and in clinical trials. For example, the utility of the compositions of the invention in the treatment of social phobia may be established e.g. by administering these to subjects who have primary DSM-III-R diagnosis of social phobia, e.g. diagnosed by using the Structured Clinical Interview for DSM-III-R, e.g. in a 12 week open clinical trial. The treatment begins e.g. using 10 mg of an active agent daily and may be increased according to clinical response and side effects. Patients complete their self-report measures at baseline and at e.g. weeks 4, 8, and 12. These measures include the fear of negative evaluation scale, social avoidance and distress scale, the social anxiety thoughts questionnaire, the fear questionnaire, the state-trait anxiety inventory, the Beck depression inventory, the social adjustment scale self-report, and the Sheehan disability scale. The responders e.g. at endpoint rate on the clinical global impression change by defining moderately or markedly improved.

The dose of the active agent in the composition of the invention is of the same order as, or up to half, that used in known compositions containing the active agent. The compositions of the invention show activity at concentrations from about 0.1 mg to about 40 mg/day of active agent, preferably from about 0.1 mg to about 20 mg/day, e.g. most preferably from about 0.1 to about 1 mg/day of active agent for respiratory disease states and from about 5 to about 10 mg/day of active agent for CNS indications for a 75 kilogram mammal.

The compositions of the invention are particularly useful for treatment and prevention of the conditions disclosed in EP 0532456B1 and EP 0707006A2, the contents of which are incorporated herein by reference, which include treatment and prevention of central nervous system disorders, including depression, dysthymia, social phobia, panic disorder, and emesis. The compositions of the invention also are useful for the treatment of respiratory diseases, e.g. asthma and chronic bronchitis. For these indications, the appropriate dosage will, of course, vary depending upon, for example, the particular composition of the invention employed, the host, the mode of administration, and the nature and severity of the conditions being treated.

A typical dose for Compound A is from 0.1 to 1 mg/day for asthma and chronic bronchitis and from 5 to 10 mg/day of active agent for depression and social phobia for a 75 kilogram mammal, for the Example 5 form.

Thus in another aspect the present invention provides a method of treatment of a subject suffering from a disorder treatable with a piperidine substance P antagonist comprising administering a therapeutically effective amount of a pharmaceutical composition of the invention to a subject in need of such treatment.

EXAMPLES

Following is a description by way of example only of compositions of this invention. Unless otherwise indicated, components are shown in % by weight based on each composition. Mean article sizes (diameters) are measured at 20° C. using a Malvern Zetasizer.

All ingredients of the Examples are given in mg/capsule.

|  | Ex 1a[1] | Ex 1b[1] | Ex 2[2] | Ex 3[2] | Ex 4[2] | Ex 5[2] | Ex 6[2] | Ex 7[2] | Ex 8[2] |
| --- | --- | --- | --- | --- | --- | --- | --- | --- | --- |
| Active Agent | | | | | | | | | |
| Compound A | 5.0 | 1.0 | 1.0 | 5.0 | 1.0 | 10.0 | 7.5 | 17.0 | 14.0 |
| 1) Surfactant | | | | | | | | | |
| Cremophor RH 40 | 232.0 | 232.0 | 269.0 | | | 225.0 | 180.0 | 200.0 | 200.0 |
| Tween 80 | | | | 269.0 | 269.0 | | | | |
| 2) Hydrophilic component | | | | | | | | | |
| Propylene carbonate | | | | | | | | 25.0 | 50.0 |
| Caprylic acid | | | | | | | | | 50.0 |
| Triethyl citrate | | | | | | | 45.0 | 50.0 | |
| Propylene glycol | 46.5 | 46.5 | | | 90.0 | 45.0 | | | |
| Polyethylene glycol 400 | | | 90.0 | 90.0 | | | | | |
| Dimethyl isosorbide | | | | | | | | 50.0 | |
| 3) Lipophilic component/ co-surfactant | | | | | | | | | |
| Labrafil 2125 | | | | 90.0 | 90.0 | | | | |
| Caprylic/capric acid glycerides (Capmul MCM) | | | | | | 170.0 | 218.5 | | |
| Propyleneglycol monocaprylate | | | | | | | | 133.0 | 136.0 |
| Miglyol 812 | | | | | | | | | |
| refined corn oil[3] | 185.0 | 185.0 | 90.0 | | | | | | |
| 4) Hydrophilic co-component | | | | | | | | | |
| Ethanol abs | 52.0 | 52.0 | 50.0 | 50.0 | 50.0 | 50.0 | 50.0 | 50.0 | 50.0 |
| Additive | | | | | | | | | |
| DL-alpha tocopherol | 0.5 | 0.5 | | | | | | | |
| TOTAL | 504.0 | 500.0 | 500.0 | 504.0 | 500.0 | 500.0 | 500.0 | 500.0 | 500.0 |
| mean particle size (nm) | 80–90 | 80–90 | 20–30 | 135–145 | 25–35 | — | — | — | — |

[1]Compound A is dissolved in (1) with stirring at room temperature and (2) and (3) are added to the obtained solution again with stirring. 0.5 ml portions of the obtained mixture are filled into size 1 hard gelatine capsules and sealed, e.g. using the Quali-Seal technique, or into soft gelatine capsules. In another embodiment of Examples 1a and 1b, Compound A is dispersed in a mixture of components 1), 2) and 3), and combined with component 4).
[2]The carrier medium is prepared by mixing the components one with another. Compound A is then dissolved in the carrier medium by stirring.
[3]Refined oil = "refined glycerol-transesterified corn oil", substantially glycerol free, as described in GB 2 257 359 and WO 94/09211.

No phase separation or precipitation is observed for any of the above compositions 1 to 8 which are clear for 4 hours.

What is claimed is:

1. An oral pharmaceutical composition in the form of a microemulsion pre-concentrate comprising (2R,4S)-N-(1-(3,5-bis(trifluoromethyl)-benzoyl)-2-(4-chlorobenzyl)-4-piperidinyl)-quinoline-4-carboxamide, at least one surfactant, a hydrophilic component, and a lipophilic component and, wherein the microemulsion pre-concentrate upon contact with an aqueous medium forms a microemulsion comprising particles having an average particle size of less than 2000 angstroms.

2. The composition according to claim 1 wherein the particles have an average particle size of less than 1.500 angstroms.

3. The composition according to claim 2 wherein the particles have an average particle size of 50 angstroms to 1,000 angstroms.

4. The composition according to claim 1 wherein the surfactant has a hydrophilic-lipophilic balance of at least 10.

5. The composition according to claim 1 wherein the surfactant is selected from the group consisting of a reaction product of natural or hydrogenated castor oil and ethylene oxide, polyoxyethylene-sorbitan fatty acid ester, polyoxyethylene fatty acid ester, polyoxyethylene-polyoxypropylene copolymer, propylene glycol mono- and di-fatty acid ester, tocopherol ester, docusate salt, phospholipid, and combinations thereof.

6. The composition according to claim 5 wherein the reaction product of natural or hydrogenated castor oil and ethylene oxide is polyethyleneglycol-hydrogenated castor oil.

7. The composition according to claim 1 wherein the hydrophilic component comprises at least one alcohol.

8. The composition according to claim 7 wherein the alcohol is selected from the group consisting of ethanol, 1,2-propylene glycol, and polyethylene glycol.

9. The composition according to claim 1 wherein the lipophilic component has a lipophilic balance of less than 10.

10. The composition according to claim 9 wherein the lipophilic component is selected from the group consisting of medium chain fatty acid triglycerides, monoglycerides, diglycerides, mixed mono-, di, and tri-glycerides, transesterified ethoxylated vegetable oils, sorbitan fatty acid esters, pentaerythriol fatty acid esters, glycerol triacetate, and combinations thereof.

* * * * *